United States Patent [19]

Lang et al.

[11] Patent Number: 4,753,231
[45] Date of Patent: Jun. 28, 1988

[54] ADHESIVE WOUND DRESSING

[75] Inventors: Stephen M. Lang, Wicken Bonhunt, Nr. Saffron Walden; David F. Webster, Bishops Stortford, both of United Kingdom

[73] Assignee: Smith & Nephew Associated Companies p.l.c., England

[21] Appl. No.: 923,307

[22] Filed: Oct. 27, 1986

Related U.S. Application Data

[63] Continuation of Ser. No. 794,753, Nov. 4, 1985, abandoned, which is a continuation of Ser. No. 516,119, Jul. 20, 1983, abandoned, which is a continuation-in-part of Ser. No. 506,501, Jun. 21, 1983, abandoned, which is a continuation-in-part of Ser. No. 396,754, Jul. 9, 1982, abandoned, which is a continuation-in-part of Ser. No. 396,732, Jul. 9, 1982, abandoned, which is a continuation-in-part of Ser. No. 345,550, Feb. 3, 1982, abandoned, which is a continuation-in-part of Ser. No. 345,488, Feb. 3, 1982, abandoned.

[30] Foreign Application Priority Data

| Feb. 13, 1981 | [GB] | United Kingdom | 8104568 |
| May 22, 1981 | [GB] | United Kingdom | 8115742 |
| Feb. 12, 1982 | [GB] | United Kingdom | 8204132 |
| Feb. 12, 1982 | [GB] | United Kingdom | 8204133 |
| Jun. 22, 1982 | [GB] | United Kingdom | 8218088 |
| Jul. 21, 1982 | [GB] | United Kingdom | 8221112 |

[51] Int. Cl.⁴ ............................................. A61L 15/00
[52] U.S. Cl. .................................... 128/156; 128/155
[58] Field of Search .............. 128/155, 156; 604/369, 604/366, 370, 375

[56] References Cited

U.S. PATENT DOCUMENTS

| 2,896,618 | 7/1959 | Schaefer | 128/156 |
| 3,566,871 | 3/1971 | Richter et al. | 128/296 |
| 3,645,835 | 2/1972 | Hodgson | 161/146 |
| 3,648,692 | 3/1972 | Wheeler | 128/156 |
| 3,678,933 | 7/1972 | Moore et al. | 128/296 |
| 3,888,248 | 6/1975 | Moore et al. | 128/156 |
| 3,927,669 | 12/1975 | Glatt | 128/156 |
| 3,972,328 | 8/1976 | Chen | 128/156 |
| 3,978,855 | 9/1976 | McRae et al. | 128/156 |
| 4,146,027 | 3/1979 | Hoey | 128/156 |
| 4,156,067 | 5/1979 | Gould | 528/73 |
| 4,181,127 | 1/1980 | Linsky et al. | 128/155 |
| 4,203,435 | 5/1980 | Krull et al. | 128/156 |
| 4,231,357 | 11/1980 | Hessner | 128/156 |
| 4,233,969 | 11/1980 | Lock et al. | 128/156 |
| 4,340,043 | 7/1982 | Seymour | 128/132 D |
| 4,341,207 | 7/1982 | Steer et al. | 128/155 |

FOREIGN PATENT DOCUMENTS

| 0050514 | 4/1982 | European Pat. Off. |
| 139942 | 1/1980 | Fed. Rep. of Germany |
| 1440191 | 6/1976 | United Kingdom |
| 2081177 | 2/1982 | United Kingdom |
| 2093702 | 9/1982 | United Kingdom |
| 2093703 | 9/1982 | United Kingdom |

Primary Examiner—C. Fred Rosenbaum
Assistant Examiner—Sharon Rose
Attorney, Agent, or Firm—Jacobs & Jacobs

[57] ABSTRACT

Moisture vapor transmitting wound dressings are described which comprise (a) a conformable backing layer which has an adhesive on one of its surfaces and in which at least one of the backing layer and adhesive layer is continuous so as to provide a barrier both to bacteria and to liquid water when the dressing is in place on a wound and (b) a low wound adherency absorbent pad positioned on the adhesive side of the backing layer. The area of the pad is less than that of the backing layer so that an adhesive margin remains exposed on two, or preferably four, sides of the pad so that the backing layer may be adhered to the skin surrounding the wound area. The wound dressings have a moisture vapor transmission rate of from 500 to 2000 grams/square meter/24 hours at 37.5° C. and 100% to 10% relative humidity difference. Materials for use in the dressings and processes for manufacture of the dressings are also described.

12 Claims, No Drawings

ADHESIVE WOUND DRESSING

This is a continuation of application U.S. Ser. No. 794,753, filed Nov. 4, 1985, which is a continuation of application U.S. Ser. No. 516,119, filed July 20, 1983 which is a continuation-in-part of application U.S. Ser. No. 506,501 filed June 21, 1983 entitled "Wound Dressing Manufacture and Use", which is a continuation-in-part of U.S. Ser. No. 396,754 filed July 9, 1982 entitled "Wound Dressing, Manufacture and Use", which is a continuation-in-part of U.S. Ser. No. 396,732 filed July 9, 1982 entitled "Wound Dressings, Manufacture and Use", which is a continuation-in-part of U.S. Ser. No. 345,550 filed Feb. 3, 1982 entitled "Wound Dressings, Manufacture and Use", which is a continuation-in-part of U.S. Ser. No. 345,488 filed Feb. 3, 1982 entitled "Wound Dressing, Manufacture and Use", all abandoned, and which applications are incorporated herein by cross-reference.

Burns and other related wounds such as donor sites and the like present a serious problem in that they tend to produce large amounts of exudate which can cause conventional dressings to become saturated or to stick to the wound or even become infected. One method of covering such wounds has been to cover the wound with a material into which new epithelial or fibroblast growth can penetrate. Dressings of this kind are disclosed in U.S. Pat. Nos. 3,526,224, 3,648,692 and 3,949,742.

However such dressings can be extremely painful to remove and often require surgical excision. A fundamentally different approach requiring a fundamentally different type of dressing is to employ materials that are designed to reduce the propensity to adhere to the wound. Dressings of this kind are disclosed in British Pat. No. 439085, French Pat. No. 947609, U.S. Pat. Nos. 3,543,750, 2,923,298 and British Pat. No. 778813 which later patents cover successfully used materials such as Melolin ("Melolin" is a registered Trade Mark of T. J. Smith & Nephew Limited, Welwyn Garden City, Hertfordshire, U.K.). One more recent attempt at non-adherent dressings is U.S. Pat. No. 3,709,221 which discloses a dressing having an outer microporous, liquid repellent fibrous layer, an inner macroporous fibrous layer and an absorbent intermediate layer which was also envisaged as normally being fibrous. In order to reduce the tendency of this material to adhere to the wound the inner layer had to be treated with an agent to render it non-wetted by body liquid. It is now realised that it would be desirable to provide a dressing in which the wound facing layer did not require special treatment. As it will become apparent hereinafter it has now been discovered that by avoiding fibrous materials it is possible to produce a dressing with reduced tendency to adhere to wounds without the need for special treatments. An attempt at producing an absorbent dressing is described in U.S. Pat. No. 3,888,748 which describes a dressing fabricated from at least four sheet materials. The wound facing part of the dressing apparently consists of a grid or scrim coated with polyethylene in such manner that the polyethylene surrounds the filaments of the grid and collects any loose thread or particle that may be present in the core material. It is now realised that it is desirable to avoid the use of wound facing layers that can allow such penetration of the central layer to the wound surface. It has also been realised that it would be desirable to provide a material that was highly conformable to the wound so that it is possible to minimise the quantity of exudate between the wound surface and the dressing. U.S. Pat. Nos. 3,709,221 and 3,888,248 disclose materials which are bonded along their edges which may reflect a desire to improve conformability. The dressing of the present invention allows for bonding over the whole operative area while retaining flexibility.

British Pat. No. 1,440,191 discloses a pervious surgical adhesive dressing which has an absorbent pad comprising a resilient foamed plastics material and a facing layer of a fibrous non woven fabric. The resilient foamed plastics materials disclosed in this patent are not hydrophilic per se and need treatment with surfactants to give them adequate absorption properties. Furthermore the discontinuous adhesive coated microporous or perforated film backing layers used in the dressing do not provide a barrier to bacteria and liquid water. British Pat. No. 1,575,830 discloses absorbent dressings including adhesive dressings which have an elastic thermoplastic backing film and an extensible absorbent layer which has an elastic reticular web facing layer. However there is no disclosure of moisture vapour transmitting dressings or the use of hydrophilic polymer foams.

It has now been found that moisture vapour transmitting adhesive conformable wound dressings can be made which have a low adherency to wounds, which are capable of absorbing large amounts of wound exudate and which profide a barrier to bacteria and liquid water.

The present invention provides a wound dressing which consists essentially of a low wound adherency wound facing layer, an absorbent layer and optionally an outer layer characterised in that the wound facing layer comprises a conformable apertured film, the absorbent layer comprises a conformable hydrophilic foam and the outer layer is either absent or is a continuous moisture vapour transmitting conformable film or is a conformable elastically extensible net or is a conformable backing layer which has an adhesive layer on one surface thereof, at least one of said backing layer and said adhesive layer being continuous to provide a barrier to bacteria and to liquid water.

The present invention provides a moisture vapour transmitting wound dressing comprising (a) a conformable backing layer which has an adhesive layer on one surface thereof, at least one of said backing layer and said adhesive layer being continuous to provide a barrier to bacteria and to liquid water and (b) a low wound adherency absorbent pad on the adhesive side of the backing layer, which absorbent pad comprises an absorbent layer of a conformable open cell foam of a hydrophilic polymer and a conformable wound facing layer of an elastomer net.

Materials for use in the dressings of the invention and methods of preparing these materials are disclosed in United Kingdom Patent Application Nos. 8204132 now published as United Kingdom Application Nos. 2093702A and 8204133 now published as United Kingdom Application No. 2093703A European Patent Applications Nos. 82300716.6 and 82300715.8, Japanese Patent Application No. 21948/82 and U.S. patent applications Ser. Nos. 345,488 and 345,550 the contents of which are incorporated herein by cross reference.

Wound dressings of the invention can suitably have a moisture vapour transmission rate of 300 to 5000 grams and preferably 500 to 2000 grams/square meter/24 hours at 37.5° C. at 100% to 10% relative humidity difference. It has been found that such moisture vapour transmission rates will allow the wound under the dressing to heal under moist conditions without causing the skin surrounding the wound to macerate.

In dressings of the invention both the conformable backing layer and the adhesive layer on one surface thereof will be moisture vapour transmitting.

The backing layer or the adhesive layer thereon can be continuous or discontinuous. However, at least one of these layers will be continuous.

In a preferred dressing of the invention both the backing layer and the adhesive layer on one surface thereof will be continuous.

The continuous moisture vapour transmitting backing layer or adhesive layer thereon of a wound dressing of the invention may be used to regulate the moisture loss from the wound area under the dressing and will also act as a barrier to bacteria and liquid water.

A preferred backing layer is a continuous conformable film. Suitable continuous conformable films will have a moisture vapour transmission rate of 300 to 5000 grams preferably 500 to 2000 grams/square meter/24 hours at 37.5° C. at 100% to 10% relative humidity difference.

Suitable moisture vapour transmitting continuous films can be made of polyurethane or copolymers of alkoxy alkyl acrylates or methacrylates such as those disclosed in British Pat. No. 1,280,631. Aptly the polyurethanes are linear polyurethanes containing polyester or polyether groups and are disclosed in U.S. Pat. Nos. 2,899,411 and 2,871,218 respectively. Favoured polyurethanes include Estanes (Trade Mark) from B. F. Goodrich. A preferred Estane is Estane 5714F. Favourably the polyurethane film will be from 12.5 to 37.5 microns thick. A 25 micron thick film of Estane 5714F has a moisture vapour transmission rate of approximately 1800 g/m$^2$/24 hours/37.5° C. at 100% to 10% relative humidity difference.

The continuous moisture vapour transmitting film can be a conformable polyurethane incompatible polymer blend film containing voids. Suitable conformable polyurethane blend films are disclosed in United Kingdom Patent Application No. GB 2081721A.

Suitable conformable discontinuous backing layers for use in the dressings of the invention can be any of those normally used for wound dressings. Such backing layers include conformable porous and microporous films, non-woven fabrics, nets and woven and knitted fabrics.

Preferred discontinuous backing layers include extensible apertured non-woven fabrics and elastomer nets. Such preferred materials are disclosed in the aforementioned patents.

Suitable adhesives which are moisture vapour transmitting as a continuous layer include various acrylate ester copolymer and polyvinyl ether pressure sensitive adhesives for example as disclosed in British Pat. No. 1280631. Favoured pressure sensitive adhesives comprise copolymers of an acrylate ester with acrylic acid for example as disclosed in United Kingdom Application No. GB 2070631.

A preferred pressure sensitive adhesive comprises a blend of high and low viscosity polyvinyl ethyl ether in particular 'adhesive composition A' disclosed in British Pat. No. 1280631. Another preferred pressure sensitive adhesive, disclosed in United Kingdom Application No. 2070631, as a copolymer of 47 parts by weight 2-ethylhexylacrylate 47 parts by weight butyl acrylate and 6 parts acrylic acid, polymerised in acetone.

Suitable discontinuous adhesive layers for use on the backing layer of dressings of the invention can be any of those conventionally used for wound dressings. Such discontinuous adhesive layers can include porous, microporous or pattern spread layers.

In dressings of the invention the absorbent pad will normally consist of a laminate of an absorbent layer of a conformable open cell foam of a hydrophilic polymer and a wound facing layer of a conformable elastomer net. The two layers in the laminate will usually be attached in a co-extensive relationship.

The conformable elastomer net of the absorbent pad of the dressing of the invention acts as a low adherency wound facing layer. This layer allows wound exudate to pass to the absorbent layer but prevents the absorbent layer making direct contact with the wound surface.

The net used in this invention is preferably an integral net that is a net with strands and junctions which have been formed integrally during manufacture.

Preferably the elastomer net is sufficiently conformable to allow the absorbent pad of the dressing to conform with the body contours and thereby maintain overall contact with the wound surface to ensure that exudate from the wound is absorbed.

It is also desirable that the elastomer net should be sufficiently elastically extensible to adjust to any dimensional changes in the absorbent layer.

Suitable elastomer nets will have an elongation at break of 100% to 800% desirably 200% to 750% and preferably 300% to 700% when measured as a 2.5 cm wide strip at a 30 cm/minute strain rate at 20° C.

Normally the elastomer net is made of a pharmaceutically acceptable water insoluble elastomer. Suitable elastomers include polyurethanes, polybutadiene and the like. Preferred polyurethane and polybutadiene elastomers are disclosed in the aforementioned patent applications.

The elastomer net of the absorbent pad of the dressing of the invention can have any convenient form depending on the chosen arrangement of strand, junctions and aperture areas and also their shapes and relative size.

Suitable forms of elastomer net for the dressings of the invention and the physical characteristics of these nets including preferred numbers and sizes of the net apertures, areas of the voids (apertures), thicknesses and weights of the net are disclosed in the aforementioned patent applications.

Most aptly the elastomer net is adapted so that the size of the net apertures in combination with the thickness of the net prevent the absorbent layer contacting the wound surface and yet will allow sufficiently rapid absorption of wound exudate to prevent pooling underneath the dressing. Suitable elastomer nets have apertures with a dimension of from 0.05 to 4 mm, more aptly from 0.05 to 2.5 or 0.05 to 2.0 mm and preferably from 0.1 to 2.5 mm. Suitable elastomer nets have a thickness of from 0.01 to 2.5 mm, typically 0.01 to 1 mm and preferably of 0.05 to 0.5 mm. Favoured elastomer nets will have 4 to 40 apertures per cm with a dimension of 0.05 to 2.5 mm. Suitably the elastomer nets used in this invention will have a weight of 10 to 80 gsm and preferably will have a weight of 15 gsm to 50 gsm.

The conformable hydrophilic polymer open cell absorbent layer used in the absorbent pad of dressings of the invention is capable of absorbing wound exudate for example from a burn. It is desirable that the hydrophilic polymer foam layer absorbs the wound exudate rapidly as this enhances the low adherency properties of the absorbent pad. Such rapid absorption prevents undesirable pooling of exudate between the dressing and the wound.

The ability of open cell hydrophilic polymer foam layers to absorb and retain fluids depends to some extent on the size of the foam cells, the porosity of the foam and the thickness of the foam layer. Apt sizes of the foam cells, cell membrane opening areas and thicknesses of the foam are disclosed in the aforementioned patent applications.

The use of such foams of hydrophilic polymer in the absorbent pad of dressings of the invention can allow the wound to be maintained in a moist condition even when the exudate produced has been absorbed and removed from the wound surface.

Suitable open cell hydrophilic foams will have a cell size of 30 microns to 700 microns and preferably a cell size of 50 microns to 500 microns. Apt open cell foams have 20% to 70% and preferably 30% to 60% of the total area of the membrane area of the cells as membrane openings. Suitably the hydrophilic foam absorbent layer will have a thickness of 0.5 mm to 20 mm, more suitably 0.8 mm to 15 mm and preferably 1 mm to 12 mm for example 2, 5 or 10 mm.

Apt foams may be polyurethane, carboxylated butadiene styrene rubber, polyacrylate or the like. Favoured hydrophilic foams are hydrophilic polyurethane and especially those which are made of crosslinked hydrophilic polyurethane. Preferred foams are made by reacting a hydrophilic isocyanate terminated polyether prepolymer with water. Favoured foams may be made from Hypol (Trade Mark) prepolymers available from W. R. Grace and Co.

In dressings of the invention the area of the absorbent pad on the adhesive side of the backing layer will be less than that of the backing layer. The absorbent pad can be suitably located on a central region of the backing layer. Such dressings can be applied over the wound and adhered to the skin on either side of a wound area by means of the exposed adhesive area of the backing layer not covered by the absorbent pad. Preferably the absorbent pad is located in a central region of the backing layer inset from the edges of the backing layer. Such preferred adhesive dressings can be adhered to the skin surrounding a wound area thereby further reducing the possibility of bacteria penetrating from the exterior of the dressing to the wound.

Conveniently the adhesive surface of the dressing can be provided with a releasable protector.

The wound dressing of the invention can contain a topically effective medicament. Most suitably the medicament is an antibacterial agent. Preferably the antibacterial agent is a broad spectrum antibacterial agent such as a silver salt for example silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as benzalkonium chloride or the like.

The medicament is preferably located in the foam layer of the absorbent pad.

Preferred amounts of suitable medicaments for incorporation into the foam layer of dressing of the invention are disclosed in the aforementioned patent applications.

The wound dressing of this invention may be in any convenient form of shape and size which is conventional for adhesive wound dressings with an absorbent pad. In a preferred form the wound dressing has a rectangular shape. In another preferred form the wound dressing can be an elongate strip which may be used as a bandage or may be used to prepare smaller dressings.

It is desirable that the wound dressing of this invention are sterile. The wound dressing of the invention is advantageously provided in bacteria impervious pouches. Such packed forms can be prepared under aseptic conditions or alternatively sterilised after packing by a conventional procedure. A favoured sterilisation procedure is heat sterilisation, for example by steam. Other favoured procedures are ethylene oxide sterilisation or gamma irradiation.

In another aspect the invention provides a process for making a wound dressing of the invention which comprises attaching (a) a low wound adherency absorbent pad which absorbent pad comprises an absorbent layer of a conformable open cell foam of hydrophilic polymer and conformable wound facing layer of elastomer net to (b) the adhesive side of a conformable backing layer which has an adhesive layer on one surface whereof, at least one of said backing layer and said adhesive layer being continuous.

The absorbent pad may be attached to the backing layer by bonding. Suitable bonding methods include heat sealing or adhesive bonding providing that the resultant adhesive layer is moisture vapour transmitting.

Conveniently the absorbent pad can be attached to the backing layer by laminating the pad to the adhesive layer.

In a continuous process the wound dressing can be made as a continuous strip in which the absorbent pad material is laminated as a strip or as separate pads to a length of adhesive coated backing layer. The continuous laminate strip can then be cut up into suitable size dressings. Conveniently a protector strip can be laminated to adhesive surface of laminate strip before it is cut into dressings.

Processes for forming the materials used in the dressings of the invention including the preferred polyurethane film backing layers, the preferred hydrophilic polyurethane foam layers, the preferred polyurethane elastomer net layers, the preferred acrylate ester copolymer and polyvinyl ethyl ether adhesive layers and laminates these materials are disclosed in the aforementioned patent applications.

The invention is illustrated by the following:

EXAMPLE 1

Moisture Vapour Transmitting Wound Dressing

A wound dressing of the invention was prepared by laminating an absorbent pad to the central region of an adhesive coated backing layer.

The backing layer was a voided polyurethane blend film (0.1 mm thick) made according to example 40 of United Kingdom Application GB No. 2081721A consisting of a blend of a linear polyurethane (60 parts by weight of Estane 58201 available from B. F. Goodrich Company) and a high impact polystyrene (40 parts by weight of a compound reference 6 MW available from R. H. Cole Limited).

The backing layer was coated with a pressure sensitive adhesive composition consisting of a copolymer of 47 parts by weight of 2-ethyl hexyl acrylate, 47 parts by weight of n-butyl acrylate and 6 parts by weight of acrylic acid polymerised in acetone according to the general method of United Kingdom Application No. GB 2070631. A dry continuous layer of adhesive at a coating weight per unit area of 28 g/m$^2$ was obtained. The adhesive coated barrier layer had a moisture vapour transmitting rate of 680 g/m$^2$/24 hrs at 37.5° C. at a 100% to 10% relative humidity difference.

An absorbent pad strip consisting of a laminate of wound facing layer of an elastomer polyurethane net (Estane 5714F available from B. F. Goodrich Company) and an absorbent layer of an open cell hydrophilic polyurethane foam (made from Hypol FHP2002 available from W. R. Grace) was made in the same manner as example 22 of United Kingdom Application No. 2093702. The polyurethane net used had a weight per unit area of 33 g/m$^2$ and had four apertures per cm of approximately 1.4 mm in size arranged in a diamond pattern. The hydrophilic foam had a thickness of approximately 2 mm.

A 5 cm wide absorbent pad strip was laminated at a central region to the adhesive face of a 15 cm wide strip of the adhesive coated backing layer. The resultant dressing strip was then provided with a silicone coated release protector (16 cm wide) which was attached to the exposed adhesive surface of the backing layer. The dressing strip was then cut into 15 cm×5 cm wound dressings of the invention.

EXAMPLE 2

Preparation of Integral Diamond Pattern Net (4 Apertures/cm)

An elastomer polyurethane net (Estane 5714F available from B. F. Goodrich) was prepared in the same manner as described in Example 22 of United Kingdom Application No. 2093702A. The resultant net was in a diamond pattern and had a weight per unit area of 33 g/m$^2$ and had 4 apertures per cm of approximately 1.4 mm in size. The net was retained on its embossing sheet for lamination to the foam.

Preparation of the Conformable Hydrophilic Polyurethane Foam Absorbent Layer Using a two component dispensing unit (Vari-o-Mix supplied by Prodef Engineering Limited) a foaming mixture was formed by mixing Hypol FHP 2002 and Brij 72 (1% aqueous solution) in the ratio of 1:2. The foaming mixture was fed into the coating head by means of an output nozzle in the form of a 15 cm 'fishtail die' and coated onto silicone coated release paper (Stearalese No. 46 available from Sterling Coated Papers Limited) by means of a knife over roller coating head set at a gap of 1 mm. The cast foam was dried by passing through an air circulating oven at a temperature of 50° C. for 5 minutes. The cast foam had a thickness of 2 mm.

Preparation of the Low Adherency Absorbent Pad

The conformable hydrophilic polyurethane foam on its silicone coated release casting paper was heat laminated to the conformable polyurethane net (4 apertures/cm) on its embossed coating sheet by passing the layers between the nip of a silicone roller and a steel roller heated by circulating oil to a temperature of approximately 135° C. The embossed sheet carrying the polyurethane net was fed in against the heated steel roller to ensure that the net was heated to its softening temperature prior to its lamination to the foam. The foam/net laminate was obtained as a strip 15 cm wide.

Preparation of Moisture Vapour Transmitting Wound Dressing

The foam/net laminate was cut into square pieces 5 cm×5 cm. The silicone coated release protector was removed from a 10 cm×10 cm moisture vapour permeable adhesive dressing comprising a continuous cast polyurethane film coated on one side with a continuous acrylic adhesive layer (as described in United Kingdom Pat. No. 1280631 and available as Op-Site Wound Dressing from T. J. Smith and Nephew Limited). A piece of the foam/net laminate was placed centrally on the adhesive coated side of the film so that the foam layer was adhered to adhesive coated film and the net-carrying side of the foam was surrounded by an exposed adhesive margin. The silicone coated release protector was replaced. The resultant dressing comprised a low adherency absorbent pad surrounded by an adhesive margin. The dressing may be packaged conventionally in a bacteria impervious pouch and sterilised by heat, ethylene oxide or gamma irradiation.

In use the dressing may be removed from the pouch, the protector removed, the net covered side of the absorbent foam placed against a wound and the exposed adhesive margin adhered to the skin surrounding the wound so as to provide a bacteria proof, liquid impervious yet absorbent and moisture vapour transmitting wound dressing.

EXAMPLE 3

Preparation of a Moisture Vapour Transmitting Wound Dressing

A foam/net laminate was prepared in a similar manner to that described in Example 2. The square pieces of foam/net laminate were adhered to an adhesive layer comprising a copolymer of 47 parts by weight of 2-ethyl hexyl acrylate, 47 parts by weight of n-butyl acrylate and 6 parts by weight of acrylic acid polymerised in acetone according to general method of United Kingdom Patent Application No. GB 2070631 spread as a continuous layer on a spun bonded polyester non-woven fabric. The foam/net laminate was placed centrally on the adhesive strip with the foam layer of the foam/net laminate adhered to the adhesive layer on the nonwoven fabric so that an exposed adhesive margin was retained around the adhesive pad. A silicone coated release protector was placed over the pad and exposed adhesive margins.

The dressing so formed may be placed in a bacteria proof pouch and sterilised in conventional manner by heat sterilisation or ethylene oxide or gamma irradiation.

DEMONSTRATION OF EFFECTIVENESS

Absorbency Testing (a) A dressing formed as described in Example 2 comprising a polyurethane backing layer 10 cm×10 cm having a pad 5.2×5.2 cm was placed with the net-carrying surface of the foam in contact with horse serum. The serum was available through an orifice 1 cm in diameter at zero hydrostatic pressure. The penetration of the serum was followed by observation and by weighing the dressing before and at intervals during the absorption process. Initially the rate of absorption was slow but increased rapidly so that, after 85 minutes from the start of the experiment, the pad was observed to be saturated and contained 8.5 g of serum, as measured by the weight difference between the start and end of the experiment.

The experiment was repeated on a similar dressing with the difference that during the initial period of absorption the pad was lightly compressed with the finger. This increase the rate of absorption, the amount of serum absorbed however was approximately the same.

The experiment showed that the absorption capacity of the foam was not restricted by the presence of a net on one surface and a film on the other.

(b) A dressing formed as described in Example 3 comprising a spun bonded polyester non-woven fabric backing layer 10 cm × 10 cm having a pad 5 cm × 5.2 cm was similarly placed in contact with horse serum. Again there was observed a slow initial absorption rate followed by a progressive increase in the rate as the pad neared saturation. This dressing showed an increase in weight of 5.35 g for 60% absorption and in a second experiment using a slightly smaller pad, 6.9 g at saturation. Again the dressing satisfactorily absorbed serum.

Moisture Vapour Permeability (MVP) Determination

Discs of the dressing material that is a laminate of net/foam/adhesive/backing layer, to be tested are clamped over Payne Permeability Cups (flanged metal cups) using sealing rings and screw clamps. The exposed surface of the test sample is 10 cm$^2$. Each cup contains approximately 10 ml of distilled water.

After weighing the cups are placed in a fan assisted electric oven maintained at 37.5°. The relative humidity within the oven is maintained at approximately 10% by placing 1 Kg of anhydrous 3-8 mesh calcium chloride on the floor of the oven.

The cups are removed after 24 hours, allowed to cool for 20 minutes and reweighed. The MVP of the test material is calculated from the weight loss and expressed in units of grams of weight per square meter per 24 hours, at 37.5° C. at 100-10% relative humidity difference.

The results were as follows:

| Sample | Moisture vapour permeability (g/m$^2$/24 hrs.) |
|---|---|
| Dressing material ex Example 2 | 865 |
| Dressing material ex Example 3 | 1145 |

What we claim is:

1. A conformable wound dressing which comprises:
   (a) a low wound adherency wound facing layer 0.05 to 1 mm thick which is a conformable elastomer net;
   (b) an absorbent layer in the form of a pad 0.5 to 20 mm thick of conformable open cell foam of a hydrophilic polymer; and
   (c) a moisture vapor permeable adhesive coated backing layer which serves to adhere the dressing to the wound area, at least one of said adhesive and said backing layer being continuous and said wound dressing having a moisture vapor transmission rate of from 300 to 5,000 grams/square meter/24 hours at 37.5° C. at 100% to 10% relative humidity difference, said wound facing layer being laminated to one face of the absorbent layer and said backing layer being laminated to the opposing face of said absorbent layer, whereby the backing layer extends beyond the absorbent layer to act as a means of retaining the dressing whereby the wound dressing prevents ingress of bacteria and liquid water to the wound which is allowed to heal under moist conditions without causing the skin surrounding the wound to macerate.

2. A dressing according to claim 1 in which both the backing layer and the adhesive layer on one surface thereof are continuous and moisture vapor transmitting.

3. A dressing according to claim 2 in which the continuous moisture vapor transmitting backing layer is a polyurethane.

4. A dressing according to claim 2 in which the continuous moisture vapor transmitting adhesive layer is an acrylate ester copolymer.

5. A dressing according to claim 1 in which the elastomer net comprises a net in which the net has intersecting diagonal strands which form a diamond pattern net.

6. A dressing according to claim 1 in which the elastomer net is formed from a polyurethane.

7. A dressing according to claim 1 in which the elastomer net has 2 to 40 apertures per cm with a dimension of from 0.5 to 4 mm.

8. A dressing according to claim 1 in which the hydrophilic polymer comprising the conformable open cell foam is a hydrophilic polyurethane.

9. A dressing according to claim 1 in which the conformable open cell foam has a cell size of 50 to 500 microns.

10. A dressing according to claim 1 in which the conformable open cell foam is a foam in which 30% to 60% of the total membrane area of the cells are membrane openings.

11. A dressing according to claim 1 in which the dressing contains a topically effective medicament.

12. A sterile wound dressing according to claim 1 within a bacteria impervious pack.

* * * * *